United States Patent [19]

Lougheed

[11] Patent Number: 5,453,417
[45] Date of Patent: Sep. 26, 1995

[54] PROCESS FOR THE PHOSPHORYLATION OF INSULIN AND PRODUCT PRODUCED THEREBY

[75] Inventor: William D. Lougheed, Toronto, Canada

[73] Assignees: The Hospital for Sick Children; The Loyal True Blue & Orange Research Institute, both of Ontario, Canada

[21] Appl. No.: 28,052

[22] Filed: Mar. 8, 1993

[30] Foreign Application Priority Data

Feb. 26, 1991 [GB] United Kingdom ............... 9104037

[51] Int. Cl.$^6$ .................... A61K 38/28; C07K 14/62
[52] U.S. Cl. .................. 514/3; 530/303; 530/344; 530/345; 530/305
[58] Field of Search ................. 530/303, 305, 530/345, 344; 514/3

[56] References Cited

U.S. PATENT DOCUMENTS

| 3,869,437 | 3/1975 | Lindsay | 514/3 |
| 4,534,894 | 8/1985 | Cerami | 530/303 |
| 4,705,845 | 11/1987 | Cerami | 530/303 |
| 5,242,900 | 9/1993 | Albisser | 530/303 |

OTHER PUBLICATIONS

Ferrel et al., *J. Am. Chem. Soc.* 70, 2102–2107, 1948.
Advanced Organic Chemistry, Ed. March, McGraw–Hill Book Co. N.Y. 1977, p. 953.

Primary Examiner—Jill Warden
Assistant Examiner—Benet Prickril
Attorney, Agent, or Firm—Neil F. Markva

[57] ABSTRACT

A process for phosphorylating a peptide comprises reacting an aqueous solution of the peptide with an effective amount of phosphorous oxychloride under conditions favoring phosphorylation of the peptide. In a specific embodiment, the peptide is insulin. A phosphorylated insulin is used in the treatment of diabetes mellitus wherein the phosphorylated insulin is produced or purified with an effective amount of phosphorus oxychloride to have substantially reduced isoelectric points and to have the property of reducing hyperglycemia without substantially inducing hypoglycemia. In a specific embodiment of the invention, the method comprises administering to a human being an effective therapeutic amount of a phosphorylated insulin essentially free of unmodified insulin and having substantially reduced isoelectric points whereby hyperglycemia is reduced substantially without inducing hypoglycemia. A phosphorylated insulin having either at least one phosphate group substituted on serine residues in the insulin or at least one phosphate group substituted on threonine residues in the insulin is for use in the treatment of diabetes mellitus.

21 Claims, 12 Drawing Sheets

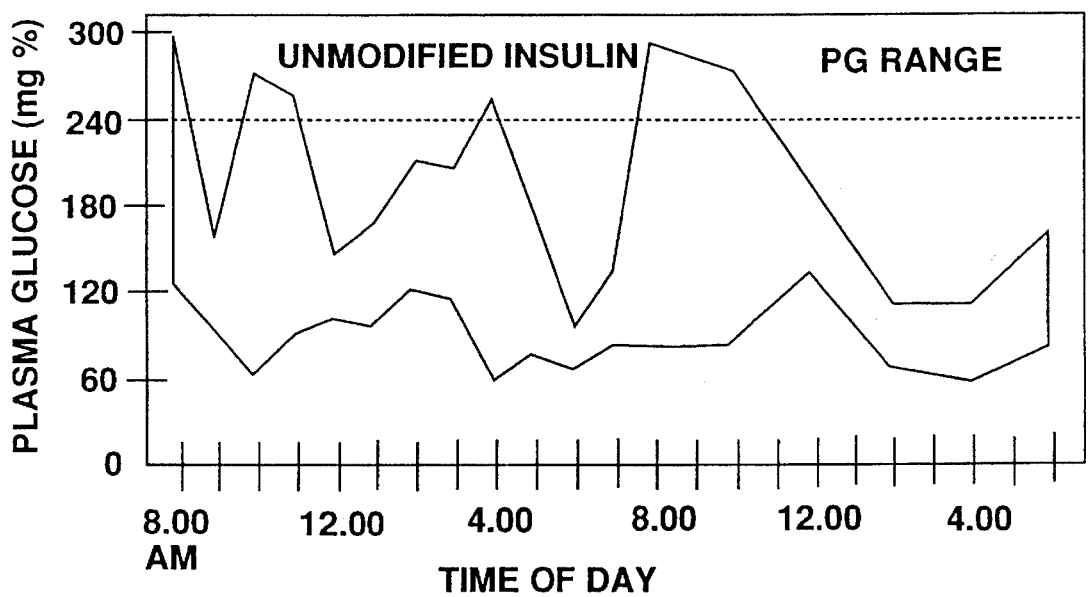
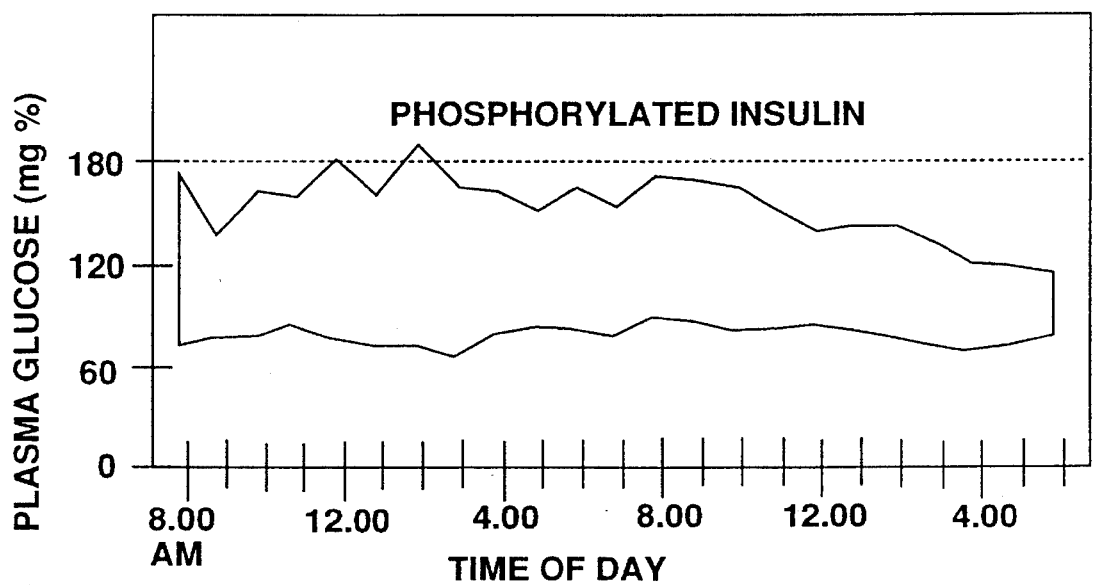

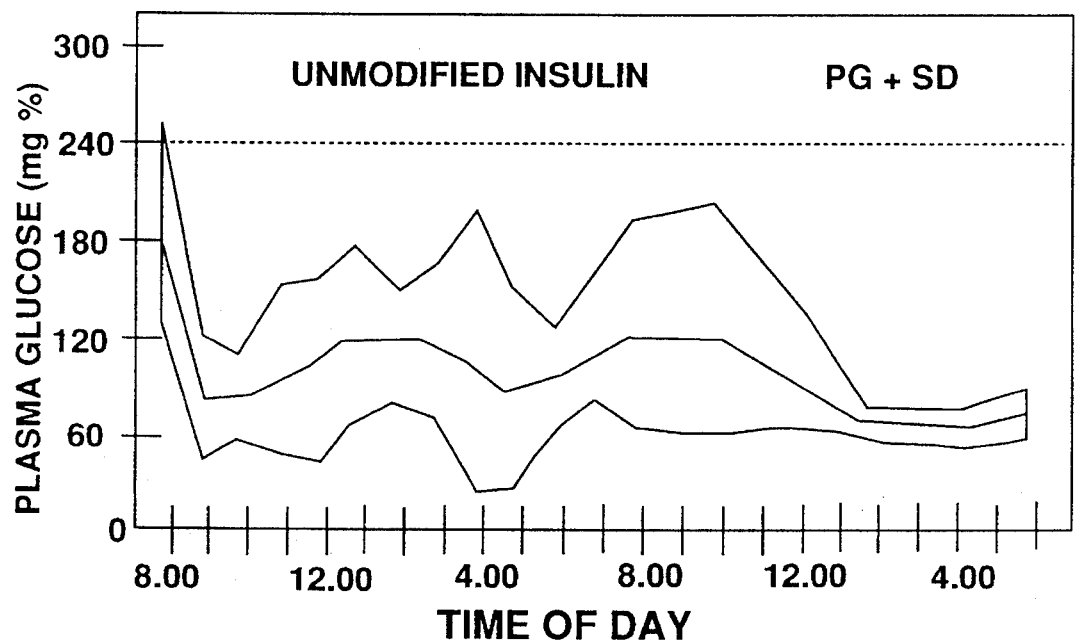

FACTOR BY WHICH INSULIN INFUSION RATE NEEDED TO BE INCREASED TO LOWER GLUCOSE FROM 100 TO 70 mg %

5,453,417

PROCESS FOR THE PHOSPHORYLATION OF INSULIN AND PRODUCT PRODUCED THEREBY

FIELD OF INVENTION

This invention relates to a novel process for the phosphorylation of insulin and to the product produced thereby, for use in the treatment of diabetes mellitus.

BACKGROUND OF INVENTION

The "therapeutic index" of a drug is defined as the "ratio between a lethal and an effective therapeutic dose". For insulin this index is extremely low (Brange, Y., in Galenics of Insulin; Springer-Verlag, N.Y., 1987). For this reason, insulin is a dangerous drug. The clinical consequence of overtreatment is coma or death. Exacerbating this delicate clinical picture is the substantial day to day variation in the rate and duration of the subcutaneous absorption of insulin (Schlichtkrull, J. et al., Handbook of Experimental Pharmacology, Hasselblatt A. (ed), vol XXXII/2,1975, Springer-Verlag, N.Y.) and this is a major cause of the large variations in blood glucose which are routinely observed in clinical practice. The many factors affecting day/day insulin absorption have been reviewed (Binder, C., Acta Pharmacol Toxicol (Copnh)(Suppl. 2) 27:1–87, 1969.; Binder, C. et al., Scand J Clin Lab Invest 19:156–63, 1967; Berger, M. et al., Diabetes Care 5:77–91, 1982; Schlichtkrull, J., et al., Acta Paediatr Scan (Suppl.) 270:97–102, 1977. Because of the combined effect of the low therapeutic index and the unavoidable variations in daily dosage, insulin therapy must be approached conservatively.

Having to approach insulin therapy conservatively makes it nearly impossible to control blood glucose within the normal range. The result is that the control of glucose and other metabolites in insulin-dependant diabetics is usually far from normal. The great weight of scientific evidence suggests that this poor glucose control is responsible for many if not all of the debilitating and potentially fatal complications of the disease. At onset the average further life expectancy of an insulin-dependant diabetic remains at 35 years, as it was some 71 years ago when insulin was discovered. The production and use of an insulin in which day to day fluctuations in absorption rate have a lesser impact on blood glucose will thus be of great benefit in the treatment and control of diabetes mellitus.

The use of certain phosphorylated insulin produces superior blood glucose control, at least in part, because a given % variation in subcutaneous absorption of the phosphorylated insulin produces a significantly lower change in blood glucose than presently available insulin.

Insulin has previously been phosphorylated by methods employing phosphoric acid (Ferrel R. E. et al., Journal of the American Chemical Society, 70, 2107–7, 1948) or phosphoric acid/POCL$_3$ in non-aqueous organic solvents using coupling agents (Cerami A. et al., U.S. Pat. Nos. 4,534,894 and 4,705,845) or with phosphoramidate (Rathlev, V. and Rosenberg T., Archives of Biochemistry and Biophysics, 65, 319–339, 1956). The phosphorylated insulin produced by Ferrel et el. and by Rathlev and Rosenberg were part of studies designed to further understand the process of phosphorylation and in particular to increase the knowledge of how it relates to biological systems. No clinical advantage of this phosphorylated insulin was observed.

The patents granted to Cerami et el. involve the production of sulfated and phosphorylated insulin that have the advantage of not polymerizing when stored long-term in insulin delivery systems. Thus, these insulins, as described by Cerami et al. have the advantage of not plugging insulin pumps and, accordingly, for the low percentage of patients using insulin pumps these insulins should produce better control of blood glucose. However, the above insulins did not exhibit physiological properties that would inherently provide better control of blood glucose, to be discussed, and thus there is no claim made to this effect.

Insulin has also been phosphorylated with POCl$_3$ with excess pyridine as disclosed by Z. Roubal et al., Chemical Abstracts, vol. 68, 1968, (Columbus, Ohio, U.S.). This reference discloses that insulin may be phosphorylated in anhydrous media with essentially no alteration of its hypoglycemic effect.

With respect to differences from the process described herein, the Cerami at al. patents emphasize that the improvement in the process is attained by conducting the phosphorylation in a non-aqueous solvent. Cerami et al. point out in (column 1, lines 39–51 of U.S. Pat. No. 4,705,845) that aqueous conditions are harsh and lead to the destruction of insulin. Accordingly, they teach that the use of sulfuric acid or phosphoric acid and a dehydrating agent in a non-aqueous apolar organic solvent effectively modifies insulin in a non-destructive manner. The process of the present invention described hereinbelow in distinction, is 1) conducted in an aqueous solvent, and 2) conducted under conditions of pH which are not harsh, and 3) produces a product which by process or by purification contains phosphorylated insulin of substantially reduced iso-electric points and which contains substantially no unreacted insulin as did the Cerami et al products (see Tables 1, 2, column 4 of U.S. Pat. No. 4,705,845). With respect to differences in product, the Cerami et al. patents claim phosphorylation only on the free hydroxyl groups of insulin (column 2, lines 29–31 of U.S. Pat. No. 4,705,845). In in the product of the present invention, the predominant phosphorylation is on the free amine groups as well as the tyrosine-OH groups and on the hydroxyl groups of serine and threenine residues.

The present invention thus relates to a product and process not only different from all known prior art, but to one in which the phosphorylated insulin so produced gives superior control of blood glucose due to significantly different pharmicokinetics. This superior ability to control blood glucose when injected subcutaneously has not been observed in any of the prior art relating to phosphorylated insulin. It is believed the improved ability to control blood glucose is at least in part due to a decreased change in blood glucose per % change in insulin dose as compared to unmodified insulin.

SUMMARY OF THE INVENTION

In its broad aspect, a process is provided for phosphorylating a peptide such as insulin comprising reacting an aqueous solution of said peptide with an effective amount of phosphorous oxychloride under conditions favouring phosphorylation of said peptide. An aqueous solution of insulin preferably is reacted with the phosphorous oxychloride at a temperature in the range of 2° to 4° C. at a pH in the range of 2 to 10, preferably 6.9 to 9.5, for a time in the range of 15 minutes to 4 hours for phosphorylation of the insulin to produce an insulin essentially free of unmodified insulin.

The process may additionally comprise dialysis or gel filtration of the phosphorylated insulin against water or suitable buffer for removing trace reactants, impurities and salt and for producing a dialysate or filtrate containing the phosphorylated insulin, preferably lyophilizing said dialysate or filtrate to produce a lyophylate, separating and purifying said lyophylate by at least one of high performance liquid chromatography, ion-exchange chromatography and preparative iso-electric focussing, and subjecting the product therefrom to at least one of gel filtration, dialysis and lyophilization.

A phosphorylated insulin for use in the treatment of diabetes mellitus is thus provided, said phosphorylated insulin produced or purified to have substantially reduced iso-electric points, preferably less than four. The phosphorylated insulin has at least one phosphate group substituted on tyrosine residues in said insulin and may be additionally phosphorylated on at least one of free amino groups in said insulin selected from the groups consisting of A1 glycine, B1 phenylalanine, B29 lysine, B22 arginine and A18, A21 and B 3 asparagine. The phosphorylated insulin may be additionally phosphorylated on at least one threonine residue and on at least one serine residue.

A method of treating diabetes mellitus in a human being is provided which comprises administering to said human being an effective therapeutic amount of a phosphorylated insulin essentially free of unmodified insulin and having substantially reduced iso-electric points. The said insulin may be administered by subcutaneous injection, intravenous infusion or injection, and can be administered intranasally or rectally.

BRIEF DESCRIPTION OF THE DRAWINGS

The process of the invention will now be described with reference to the accompanying drawings, in which:

FIGS. 1–4 are graphs which demonstrate the superior control of blood glucose achieved with phosphorylated insulin in diabetic dogs;

DETAILED DESCRIPTION OF THE INVENTION

Figure 1A:
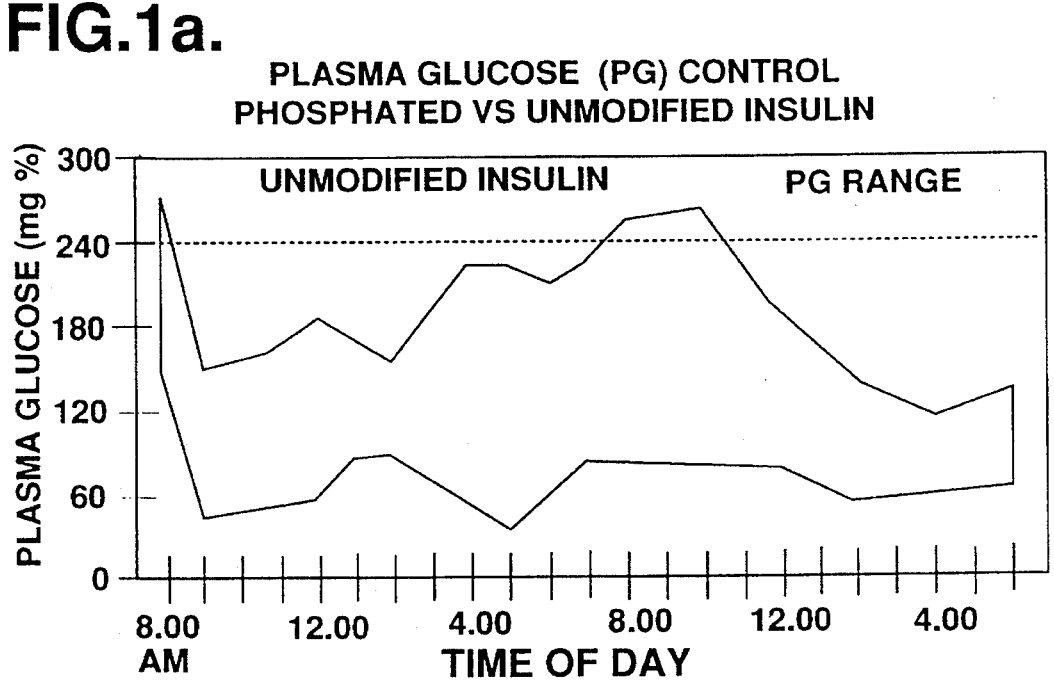

In accordance with the process of the present invention, insulin is phosphorylated by contact with phosphorous oxychloride in an aqueous solution. Peptides or proteins which are phosphorylated by such contact contain amino ($NH_2$) or hydroxyl (OH) groups. The reaction with insulin, when conducted at alkaline pH, and as described in the following examples, favours phosphorylation on the free amino groups in insulin and on the OH groups of tyrosine, serine and threonine in insulin. The phosphorylation of the tyrosine residues of insulin markedly increases as the pH of the reaction is raised above 9.0 as observed by a substantial decrease in absorbance at 276 nm when the reaction is conducted at pH 9.0–9.5. Dephosphorylation of the serine and threonine residues occurs upon storage at neutral and alkaline pH so that the extent of the threonine and serine phosphorylation progressively decreases in the products described herein. Phosphate esters of serine and threonine are unstable at alkaline pH and are stable at acid pH while the converse is true for phospho-amino derivatives of amino acids. Storage at pH 2.0–3.0 at 4° or 22° C., for example, increases this rate of dephosphorylation of the phosphorylated insulin described herein by 4–5 fold, indicating that free amino groups are phosphorylated by the present process described herein. The pertinent phosphorylated insulin also dephosphorylates at alkaline pH (e.g. 9.0) indicating dephosphorylation of serine, threonine hydroxyl groups. Phosphorylated insulin described herein show absorption bands that clearly demonstrate phosphorylation of: 1) aliphatic hydroxyl groups (serine and threonine), 2) aromatic hydroxyl groups (tyrosine) and 3) free amino groups.

For pork insulin the free hydroxyl groups are A8 and B27 threonine and A9, A12 and B9 serine; the aromatic hydroxyl groups are A14, A19, B16, B26 tyrosine; and the free amino groups encompass A1 glycine, B1 phenylalanine, B22 arginine, B29 lysine, and A18, A21, B3 asparagine. This is shown in Table 1 along with the amino acid composition of other pertinent insulins including human insulin. For human and pork insulin the sites of phosphorylation for both are identical except that human insulin contains one additional threonine at position B30.

TABLE 1

| | PORK | | HUMAN | | BEEF | | RAT 1 | | RAT 2 | |
|---|---|---|---|---|---|---|---|---|---|---|
| | A | B | A | B | A | B | A | B | A | B |
| 1 | GLY | PHE | GLY | PHE | GLY | PHE | GLY | PHE | GLY | PHE |
| 2 | ILE | VAL | ILE | VAL | ILE | VAL | ILE | VAL | ILE | VAL |
| 3 | VAL | ASN | VAL | ASN | VAL | ASN | VAL | LYS | VAL | LYS |
| 4 | GLU | GLN | GLU | GLN | GLU | GLN | ASP | GLN | GLU | GLN |
| 5 | GLN | HIS | GLN | HIS | GLN | HIS | GLN | HIS | GLN | HIS |
| 6 | CYS | LEU | CYS | LEU | CYS | LEU | CYS | LEU | CYS | LEU |
| 7 | CYS | CYS | CYS | CYS | CYS | CYS | CYS | CYS | CYS | CYS |
| 8 | THR | GLY | THR | GLY | THR | GLY | ALA | GLY | ALA | GLY |
| 9 | SER | SER | SER | SER | SER | SER | SER | PRO | SER | SER |
| 10 | ILE | HIS | ILE | HIS | VAL | HIS | ILE | HIS | ILE | HIS |
| 11 | CYS | LEU | CYS | LEU | CYS | LEU | CYS | LEU | CYS | LEU |
| 12 | SER | VAL | SER | VAL | SER | VAL | SER | VAL | SER | VAL |
| 13 | LEU | GLU | LEU | GLU | LEU | GLU | LEU | GLU | LEU | GLU |
| 14 | TYR | ALA | TYR | ALA | TYR | ALA | TYR | ALA | TYR | ALA |
| 15 | GLN | LEU | GLN | LEU | GLN | LEU | GLN | LEU | GLN | LEU |
| 16 | LEU | TYR | LEU | TYR | LEU | TYR | LEU | TYR | LEU | TYR |
| 17 | GLU | LEU | GLU | LEU | GLU | LEU | GLU | LEU | GLU | LEU |

TABLE 1-continued

| | PORK | | HUMAN | | BEEF | | RAT 1 | | RAT 2 | |
|---|---|---|---|---|---|---|---|---|---|---|
| | A | B | A | B | A | B | A | B | A | B |
| 18 | ASN | VAL | ASN | VAL | ASN | VAL | ASN | VAL | ASN | VAL |
| 19 | TYR | CYS | TYR | CYS | TYR | CYS | TYR | CYS | TYR | CYS |
| 20 | CYS | GLY | CYS | GLY | CYS | GLY | CYS | GLY | CYS | GLY |
| 21 | ASN | GLU | ASN | GLU | ASN | GLU | ASN | GLU | ASN | GLU |
| 22 | | ARG | | ARG | | ARG | | ARG | | ARG |
| 23 | | GLY | | GLY | | GLY | | GLY | | GLY |
| 24 | | PHE | | PHE | | PHE | | PHE | | PHE |
| 25 | | PHE | | PHE | | PHE | | PHE | | PHE |
| 26 | | TYR | | TYR | | TYR | | TYR | | TYR |
| 27 | | THR | | THR | | THR | | THR | | THR |
| 28 | | PRO | | PRO | | PRO | | PRO | | PRO |
| 29 | | LYS | | LYS | | LYS | | LYS | | MET |
| 30 | | ALA | | THR | | ALA | | SER | | SER |

As the extent of the reaction of phosphorylation according to the present process is increased, the product shows the following changes in absorption spectra: 1) a progressive decrease in the UV range, specifically at 276 nm indicating tyrosine phosphorylation, 2) a progressive increase in the absorption in the IR range, specifically at 10.7 and 11.45 um (phosphorylation of free amino groups), and 3) a progressive increase in absorption at 990 $cm^{-1}$ (phosphorylation on serine and threonine hydroxyl groups).

Unlike previous aqueous reactions, this process permits the use of mild pH conditions coupled with temperature and time constraints such that these conditions are ones in which insulin is stable.

The preferred reaction involves the slow addition of $POCL_3$ to a solution of insulin with the pH of said reaction being maintained between 2 and 11 and more preferably between pH 6.5 and 9.5. It is further preferred that a buffer or buffers be used to adequately control the pH. Citrate, acetate or glycine are preferred buffers when the reaction is conducted at acid pH while phosphate, glycine, TRICINE™ and HEPES™ are preferred at alkaline pH. The pH can be controlled by the addition of base during the reaction but this makes the process more difficult.

The preferred reaction temperature is 0°–4° C. Optimal reaction times may vary from 15 minutes to 4 hours but are not constrained to these limits depending upon the rate of $POCL_3$ addition. The concentration of $POCL_3$, pH, reaction time and temperature control the extent of phosphorylation.

The preferred reaction involves performing the reaction with sufficient $POCl_3$ and/or for a sufficient length of time (for a given temperature), so as to produce a phosphorylated insulin such that the majority of phosphorylated products have iso-electric points that are substantially reduced from the iso-electric point of unmodified insulin (the latter being 5.3–5.6 depending upon species of origin). It further embodies the purification of phosphorylated insulin and the isolation of only those portions which have substantially reduced iso-electric points. It further, involves the production by either process and/or purification of phosphorylated insulins in which all of the unmodified insulin has been removed. The removal of the unmodified insulin (which the Cerami et al patent did not teach) is necessary as unmodified insulin negates the benefit obtained from the gentler pharmicokinetic properties of the phosphorylated insulin described herein.

Insulin of animal origin, or produced by recombinant methods, may be phosphorylated in the above manner.

For subcutaneous injection, the duration of action can be prolonged by the addition of protamine and/or zinc.

A further embodiment of this process is the addition of salts such as sodium chloride or sodium phosphate and preservatives such as m-cresol, methylparaben or phenol to the formulation.

The phosphorylated insulin described herein dephosphorylates upon storage in aqueous media. The addition of chelators such as EDTA stabilize these products against dephosphorylation. The addition of salts such as sodium chloride and sodium phosphate inhibit dephosphorylation, but at concentrations of 25 mM to 0.5M are only partially effective.

The examples described below exemplify the process and product of the invention, its use and its efficacy, but are by no means meant to limit its scope.

EXAMPLE 1

40 mg of monocomponent porcine insulin was dissolved at pH 2.5 in deionized distilled water (10 ml). The pH was raised to 7–9 with the addition of 0.268 g of $Na_2HPO_4 \cdot 7H_2O$ or with 10N NaOH (rapid stirring during addition). The mixture was cooled to 0°–2° C. in a dry ice/ice/EtoH bath. 175 μl of $POCl_3$ precooled to 0°–2° C. was added dropwise at a constant rate over a period of 80 minutes. The pH of the constantly stirred reaction mixture was rocked between pH 6.5 and 9.5 by the intermittent dropwise addition of 0°–2° C. 10N NaOH. The temperature of the reaction mixture was maintained between 0° and 4° C. during $POCl_3$ addition. At 80 minutes, 0.92 g of trishydroxyaminomethane TRIS™ buffer was added to the reaction mixture. The pH was controlled between 7 and 8 over the subsequent 40 minutes by the dropwise addition of 0°–2° C. 10N NaOH while the reaction mixture was allowed to warm to room temperature. The product was dialysed to equilibrium at 4° C. against repeated changes of 2.3 g/l NaCl or deionized, distilled $H_2O$ with the prior addition of m-cresol to 0.25% v/v to the dialysate.

EXAMPLES 2, 3, 4, 5, 6

These reactions were conducted exactly as Example 1 but with changing the amount of $POCl_3$ added as follows: (a) 350 μl $POCl_3$ (Example 2); (b) 240 μl $POCl_3$ (Example 3); (c) 100 μl $POCl_3$ (Example 4); (d) 50 μl $POCl_3$ (Example 5); and (e) 600 μl $POCl_3$ (Example 6).

EXAMPLE 7

This process was conducted under the conditions of Example 1 but with the omission of the sodium phosphate buffer.

EXAMPLE 8

This reaction was performed as in Example 1 but TRIS™ buffer was not added. The pH was controlled as above but with the use of 10N NaOH only.

EXAMPLE 9

This process was performed as in Example 2 but the reaction mixture was kept at 0°–4° C. for 4 hours after $POCl_3$ addition at which point the pH had stabilized and the reaction was complete.

EXAMPLE 10

This reaction was performed as in Example 2 but human insulin was used in the place of porcine insulin.

EXAMPLE 11

This reaction was performed as in Example 1 but bovine insulin was used.

EXAMPLE 12

This reaction was performed as in Example 2 but zinc-free sodium insulin was used.

EXAMPLE 13

Insulin was produced as described in Example 3 and reconstituted at pH 7.2–7.4 in 25 mM phosphate buffer containing 0.25/m-cresol as a preservative and the solution made isotonic with NaCl.

EXAMPLE 14

Insulin was produced as described in Example 2 and reconstituted at pH 7.2 in 150 mM phosphate buffer containing 0.25% m-cresol and the solution made isotonic with NaCl.

EXAMPLE 15

Insulin was produced as described in Example 13 but protamine was added to the phosphorylated insulin to give a 6:1 molar ratio of insulin to protamine.

EXAMPLE 16

Insulin was produced as described in Example 12 but protamine was added to give a 1:1 molar ratio of insulin to protamine.

EXAMPLE 17

This formulation was prepared as described in Example 16 but in addition zinc acetate was added to give a total $Zn^{2+}$ concentration of 0.1 mg/ml.

EXAMPLE 18

This formulation was prepared as described in Example 17 but with the omission of protamine. $Zn^{2+}$ was present in a concentration of 0.1 mg/ml to provide protracted effect.

EXAMPLE 19

Exactly as Example 1 but $POCl_3$ was added in equal amounts at 5 minute intervals.

EXAMPLE 20

The products so obtained by the above processes described in Examples 1–19 were analysed by iso-electric focussing on a BIORAD™ mini-IEF cell using 4% polyacylamide gels containing 3.5 and/or 5/7 ampholytes (Bio-Rad) to establish pH gradients. The iso-electric points of the products ranged between 2.1 and 5.2. Ten phosphorylated insulins of increasing degree of phosphorylation were identified. The degree of phosphorylation and the heterogeneity of the product could be controlled by varying reactant concentrations and reaction time and temperature.

The different phosphorylated products could be separated by fractionation using ion exchange chromatography, in particular on A25 Sephacel using a linear NaCl gradient from 0 to 0.4M in the pH range of 5.0 to 7.5.

EXAMPLE 21

The number of phosphate groups introduced per insulin molecule could be controlled by varying the amount of $POCl_3$ added in the reaction, as shown in Tables 2–3. As shown in Table 2, 100 µl of $POCl_3$ (Example 4) gave a product in which the predominant species had an iso-electric point (pI) of 4.7 corresponding to the introduction of 1.8 phosphate groups/insulin monomer. Increasing the amount of $POCl_3$ as per the method of Example 2 produced a phosphorylated insulin in which 55% of the product has a pI of 3.5 (5 phosphate groups/insulin monomer). In this manner, phosphorylated insulin containing between 1.1 and 11.3 phosphate groups could be produced as shown in Table 3.

TABLE 2

% Of Total Product Having Those Iso-Electric Points (pI) Shown In Brackets, Plotted For Various amounts of $POCl_3$ Used In the Reaction.

| $POCl_3$ (µl) | % of Product And pI (in brackets) |
|---|---|
| 100 (Example 4) | 2, (4.1); 6, (4.3); 10, (4.5); 39, (4.7); 31, (4.9); 10, (5.35) |
| 240 (Example 3) | 8, (3.5); 36, (3.7); 29, (3.9); 16, (4.1); 3, (4.3); 3, (4.5); 5, (4.9) |
| 350 (Example 2) | 7, (3.1); 55, (3.5); 21, (3.9); 11, (4.1); 6, (4.4) |
| 600 (Example 6) | 17, (2.2); 21, (2.6); 27, (3.1); 29, (3.3); 6, (3.5) |

TABLE 3

| Iso-Electric Point (pI) | Average number of Phosphate Groups/ Insulin Monomer |
|---|---|
| 2.2 | 11.3 |
| 2.6 | 7.9 |
| 3.1 | 6.0 |
| 3.3 | 5.5 |
| 3.5 | 5.0 |
| 3.7 | 4.4 |
| 3.9 | 4.1 |
| 4.1 | 3.6 |
| 4.5 | 2.7 |
| 4.7 | 1.8 |
| 4.9 | 1.1 |

EXAMPLE 22

Increasing the amount of $POCl_3$ produced a progressive decrease in absorption at 276 nm proving that progressive phosphorylation of the tyrosine residues occurs with increasing $POCl_3$. The products as per Examples 3, 2, 6 respectively gave absorption at 276 nm of 82%, 53% and 35% that of unmodified insulin. This shows that an average of 1 tyrosine residue was phosphorylated using 240 μl $POCl_3$ (as per Example 3) and this increased to an average of 3 phosphorylated tyrosine residues when the reaction was conducted as per Example 6.

EXAMPLE 23

Figure 9:
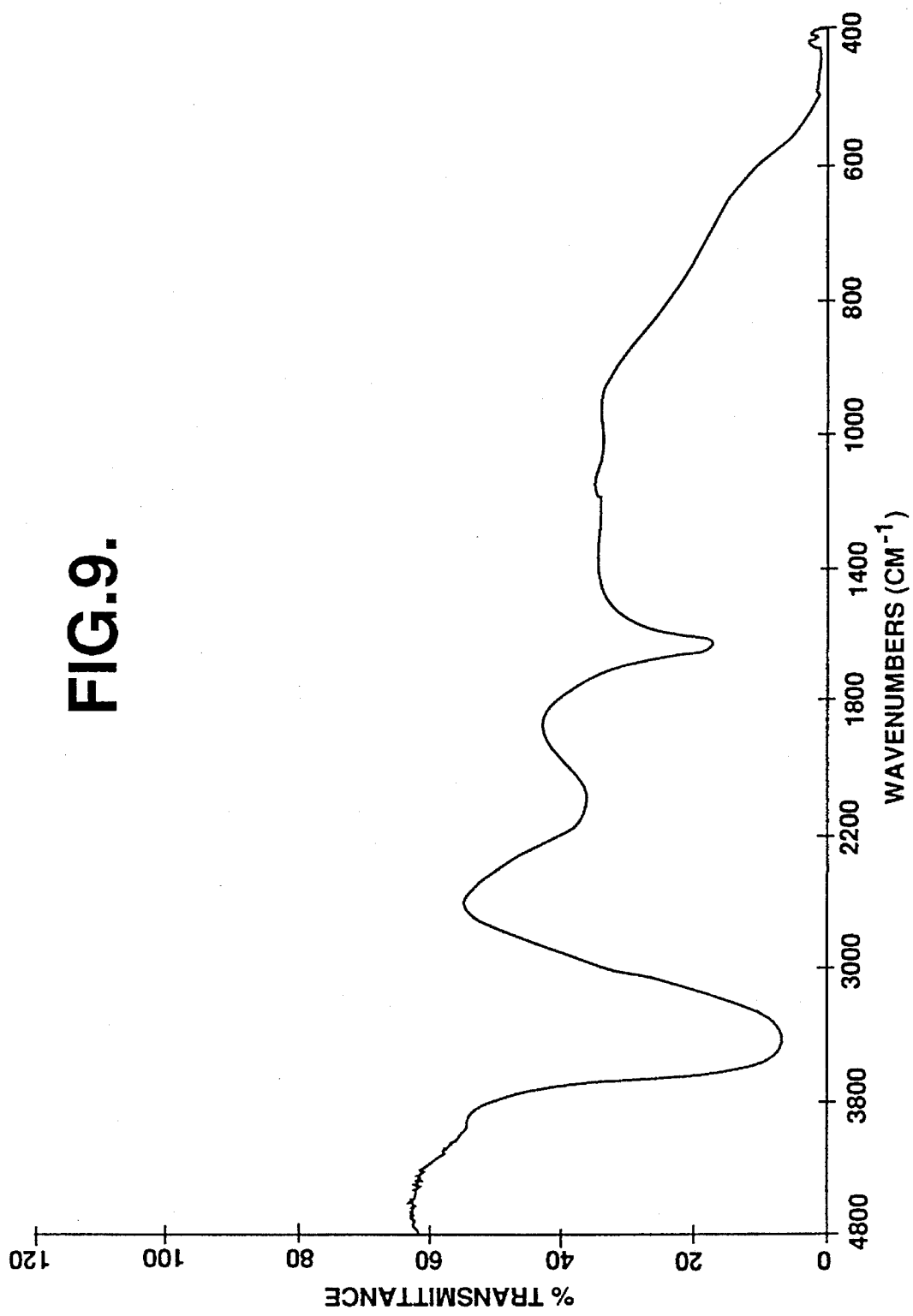
FIGS. 9 and 10 are graphs which show, respectively, the infra-red spectra of regular and phosphorylated insulin.
Figure 10:
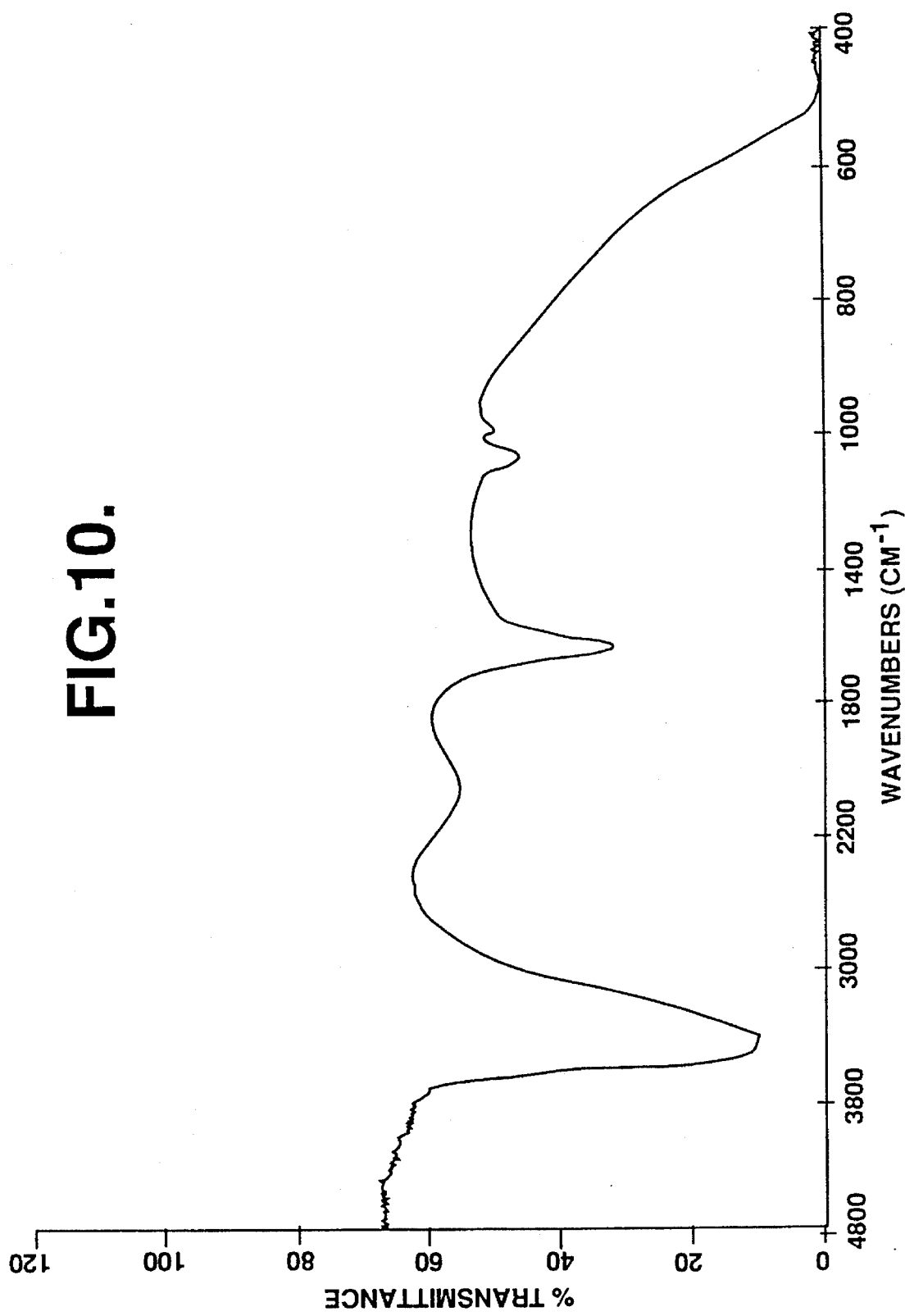
Figure 11:
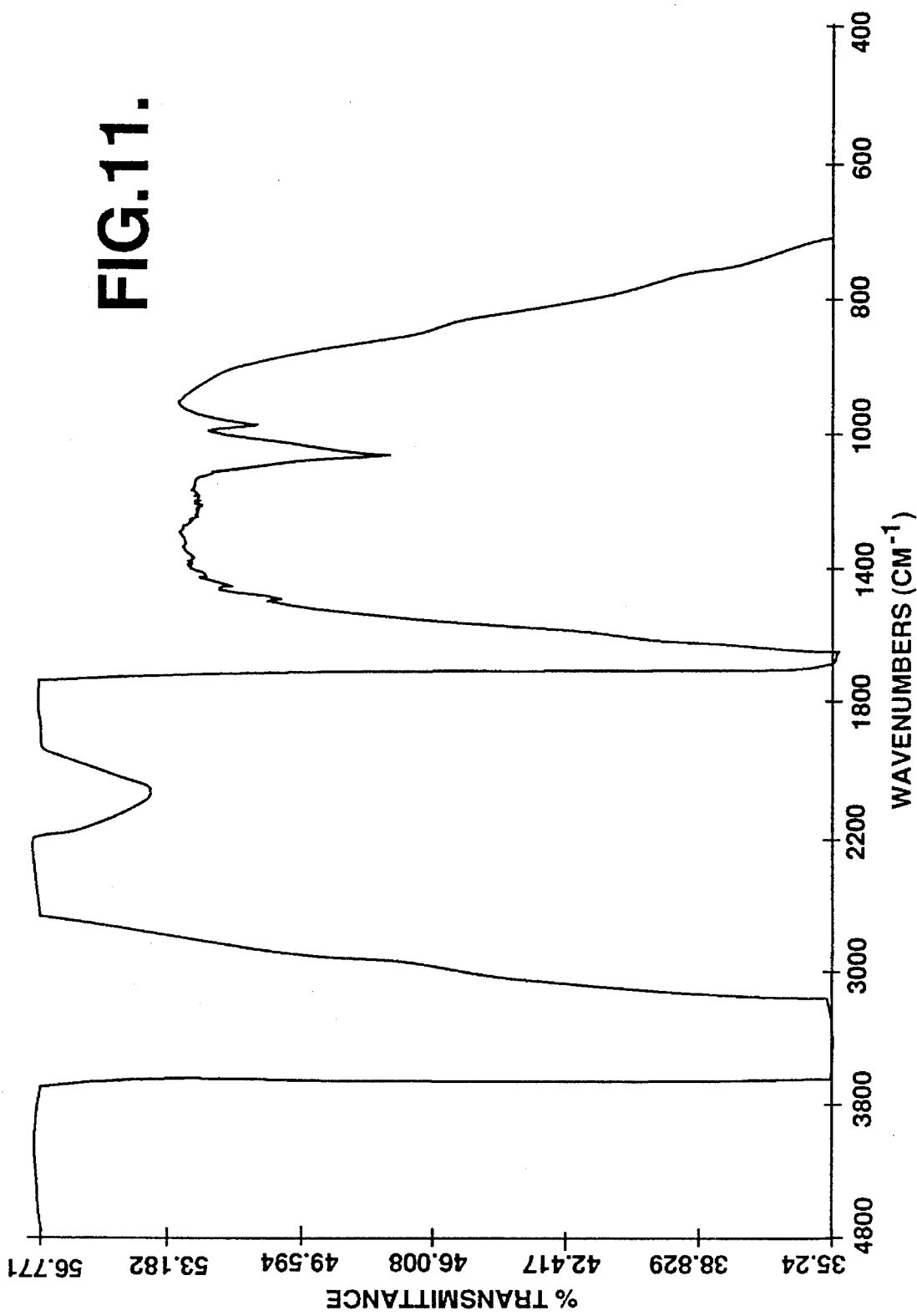
FIG. 11 is a graph which is an enlargement of FIG. 10.

Fourier transform infra-red (FTIR) spectroscopy was performed on products produced as per Examples 2, 3 and 6. A decrease in transmittance (increase absorption) was observed at 990 $cm^{-1}$ ($CH_2OP \rightarrow O$ bond, i.e. Serine and Threonine in insulin) and at 1,060 $cm^{-1}$ (aryl phosphate i.e. Tyrosine). The FTIR spectra for Example 4 phosphorylated product is shown in FIGS. 10 and 11 and that for unmodified insulin is shown in FIG. 9. $CH_2OPO$ bond stretching may be contributing to the absorption peak at 1,060 $cm^{-1}$ as its absorption peak spans 900–1,050 $cm^{-1}$.

EXAMPLE 24

Products as per Examples 2, 3 and 6 show absorption on FTIR at 925–940 $cm^{-1}$ indicating N—P bond formation and accordingly phosphorylation of amino groups in insulin. An increase in absorption could not be detected for the product in which only 100 μl of $POCl_3$ was used. Phosphorylated insulin gave a progressively less positive reaction for ninhydrin as the extent of phosphorylation was increased. This data demonstrate that progressive phosphorylation of the free amino groups in insulin occurs as the amount of $POCl_3$ is increased.

EXAMPLE 25

As determined by iso-electric focussing (I.F.), all of the phosphorylated products produced in the above examples dephosphorylated upon storage at 4° C. or 22° C. in $H_2O$ at either (a) pH 3.0 or (b) pH 9.0. As phosphate esters are in general stable at acid pH and N-phosphate compounds stable at alkaline pH, this data indicate dephosphorylation of amino groups and phosphate esters (serine and threonine).

EXAMPLE 26

The above dephosphorylation could be progressively inhibited by the addition of salt and, thus, sodium chloride and sodium phosphate in concentrations of 25 mM to 0.5M showed this effect. However, the inhibition was not total and dephosphorylation was observed at 22° C. after 8 days storage in solutions as described in this example.

EXAMPLE 27

Chelators effectively bind free metal ions. Free metal ions are known to bind to phosphate and known to catalyze dephosphorylation.

Solutions of phosphorylated insulin as described herein, when stored at pH 7–9 in solutions containing 50 mM of the chelator ethyldiamine-tetra-acetic acid (EDTA) showed remarkably increased stability visa vi dephosphorylation. Solutions of phosphorylated insulin containing 50 mM EDTA and 25 mM–150 mM NaCl or sodium phosphate at pH 7–9 showed no dephosphorylation after 60 days storage at 22° C.

EXAMPLE 28

Phosphorylated insulin produced in examples 2, 3, 4 and 6 were purified and separated into their individual components using ion exchange chromatography. DEAE sephadex or sephacel or similar gels could be used but the best separation was achieved on Q Sepharose Fast Flow™. Separation was performed at pH 6.5–8.5 at 4°–22° C. However, optimal separation was achieved using the following conditions: 15 mM BISTRIS™ pH 6.5, 15 ml/hr 4° C., 0.1–0.35 M NaCl gradient.

The product could also be purified using preparative iso-electric focussing. For this a ROTOFOR™ IEF preparative cell was used. 3/5 and/or 5/7 ampholytes were employed to establish the pH gradient. Separations were conducted at 800–2,000 volts for 2–6 h.

EXAMPLE 29

Partial purification could be achieved on HPLC using gradients containing acetonitrile.

EXAMPLE 30

Long acting and short acting phosphorylated insulin produced by the above methods containing product purified or produced so as to have a substantial portion of the material with iso-electric points below four was administered by subcutaneous injection to diabetic dogs over the course of 2 months.

Dogs serving as their own controls were then switched to an identical regime but using unmodified commercially available long and short acting insulin.

Figure 1B:
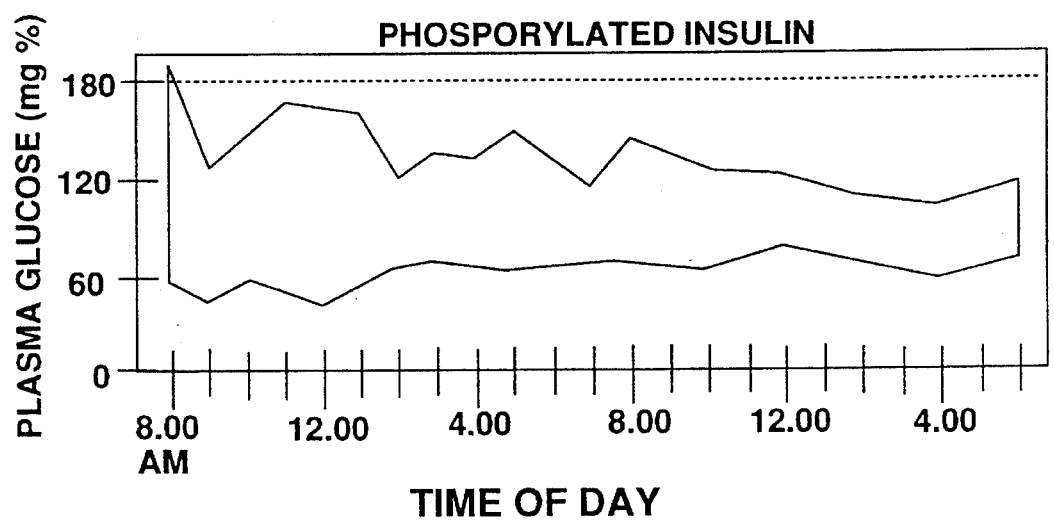

Blood glucose was monitored 24 hours per day. Thirty-six experiments of 24 hour duration were performed on each dog. Dogs were fed 3 meals of equal caloric contents (340 Kcal) at 8 a.m., 12 p.m. and 4 p.m. on all experimental days. Dogs were injected with short acting insulin at 8:30 p.m., 12:30 p.m., 4:30 p.m. and with long acting insulin at 8:30 a.m. and 10:30 p.m. The range of blood glucose values observed for dogs receiving phosphorylated insulin was significantly less than observed with unmodified commercially available insulin as shown in FIGS. 1 and 2.

Figure 4A:
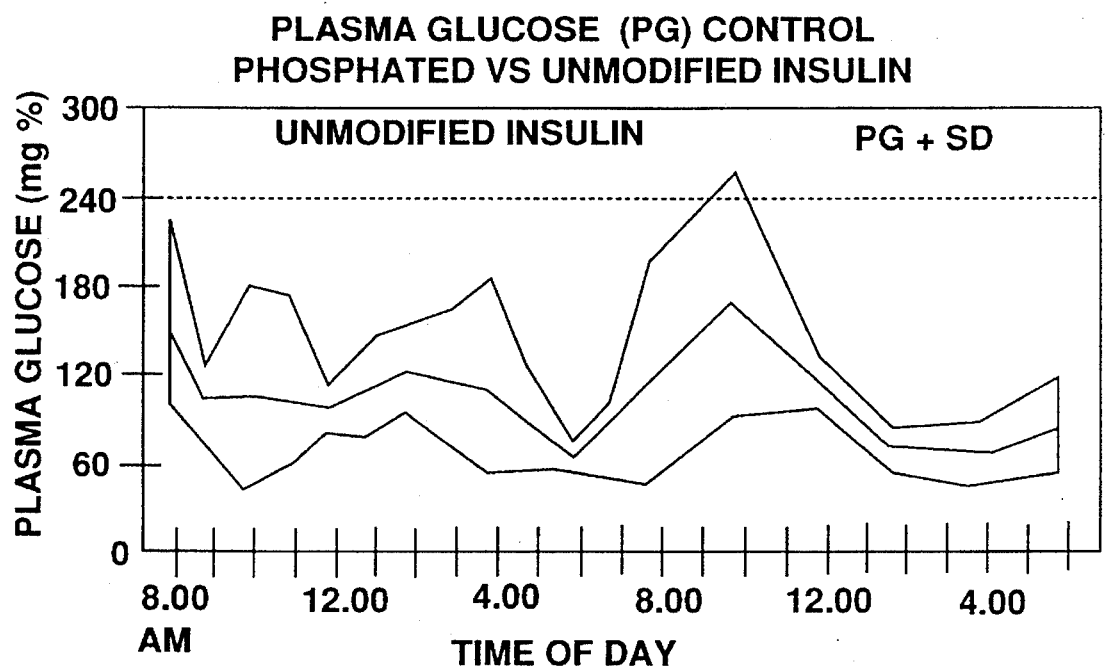
Figure 4B:
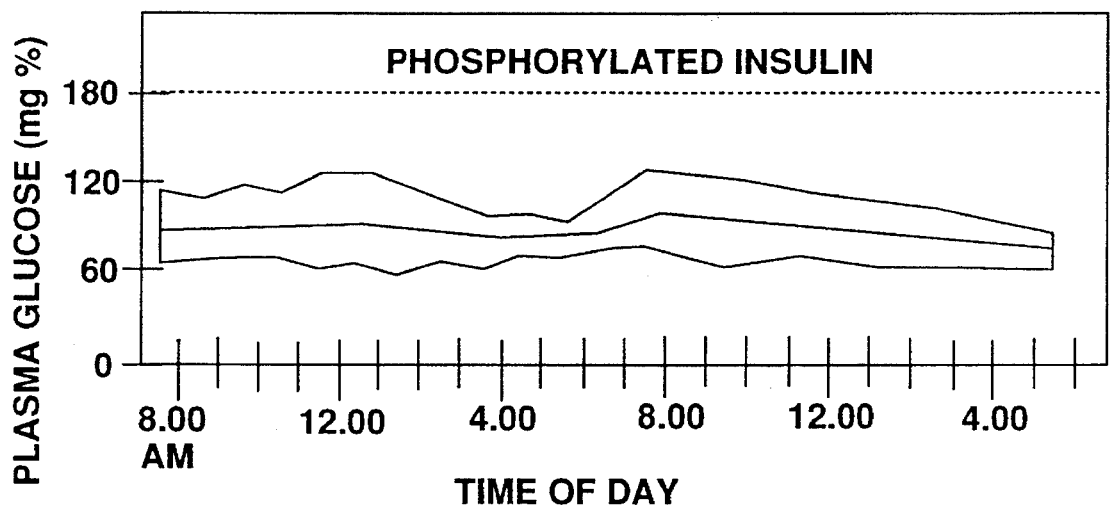

As shown in FIGS. 3 and 4, blood glucose was significantly closer to the normal range for animals treated with phosphorylated insulin. This improvement in control was statistically significant for 21 out of the 24 time points during the day ($p<0.05$). The mean plasma glucose (solid line) and standard deviation (SD, shaded area) are shown in these figures.

EXAMPLE 31

Figure 5:
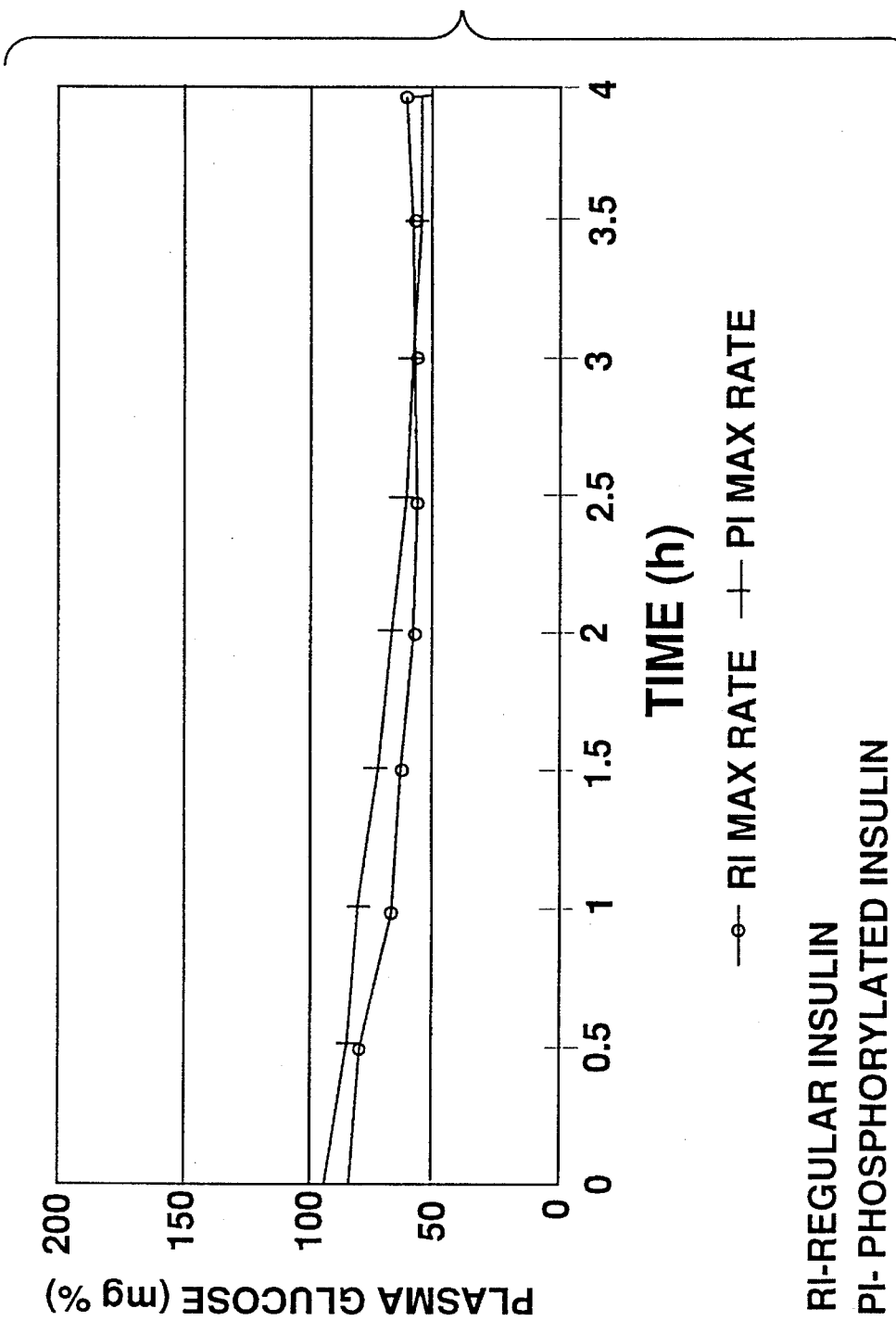
FIGS. 5–7 and FIG. 12 are graphs which demonstrate the smaller change in blood glucose that results with phosphorylated vs regular insulin when the insulin infusion rate is varied by a specified amount in diabetic dogs.

This example relates to the continuous 24 hour day infusion of phosphorylated insulin produced by the process described in Example 3 (produced and purified to contain substantially reduced average iso-electric pt.) into 4 diabetic (pancreatectomized) dogs. The initial step in the protocol involved determining the required insulin infusion rate of either regular or phosphorylated insulin that would, under fasting conditions, reduce plasma glucose from normal at 7:30 a.m. to a plateau of 60 mg %, 2–4 hours later. As shown in FIG. 5, this was achieved for both phosphorylated and regular insulin with the plateau of 60 mg % extending over the last 2 hours of the experiments. There was no significant difference between the glucose plateau achieved with each insulin. The rate that produced this reduction of blood glucose to 60 mg % was termed "Max Rate".

Figure 6:
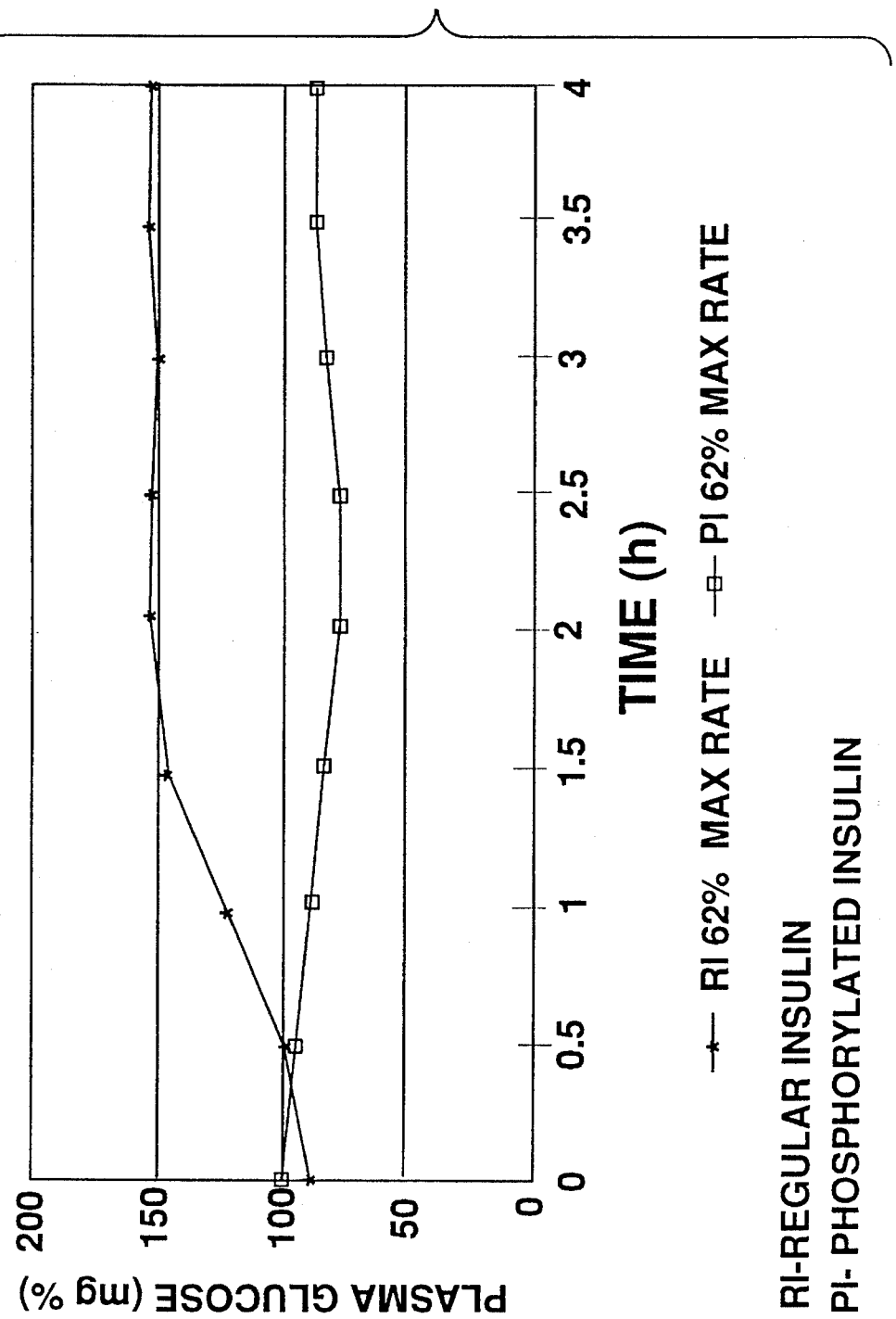
Figure 7:
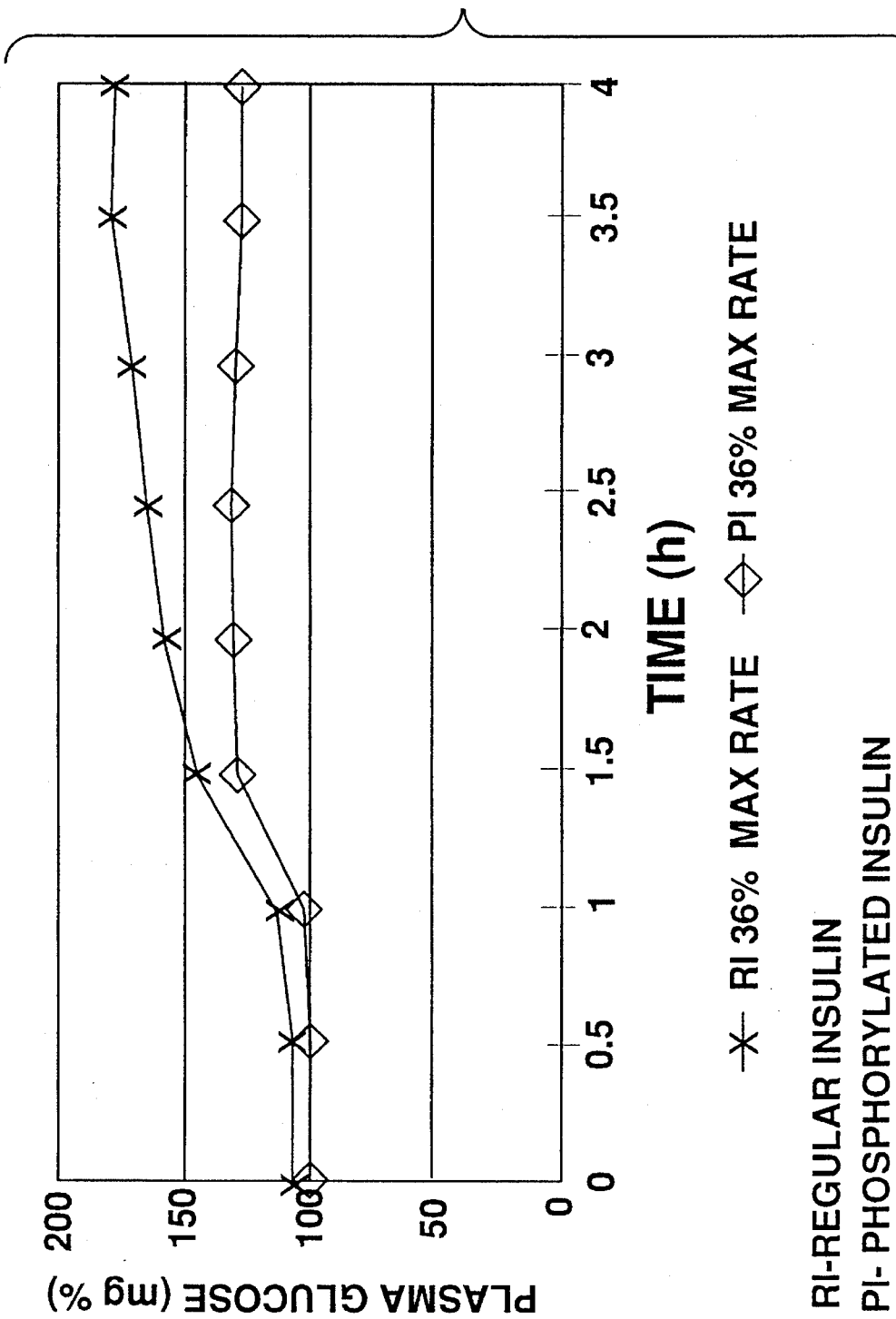

On subsequent days, identical experiments were conducted on all 4 diabetic dogs with the exception that the animals received a reduced rate of insulin infusion equal to either 1) 62% of the "Max Rate" as shown in FIG. 6 or 2) 36% of the "Max Rate" as shown in FIG. 7. As demonstrated in FIG. 6, a reduction in the infusion rate of regular insulin to 62% caused the dogs' glucose to rise to an average plateau of 150 mg %. The same reduction in infusion rate of phosphorylated insulin resulted in a plateau of 80–85 mg % (FIG. 6).

Similar results were obtained when the rate was further reduced to 36% of the "Max Rate" as is shown in FIG. 7. In this test, the dogs infused with regular insulin reached a glucose threshold of 180 mg % (renal threshold at which the kidneys begin to spill glucose into the urine). The phosphorlated infused dogs reached a lower average glucose level of 120–130 mg %.

This example serves to demonstrate the lower resulting change in blood or plasma glucose that results from a given change in insulin dosage when compared with regular insulin. All protocols described were conducted in triplicate on all dogs.

EXAMPLE 32

Figure 8:
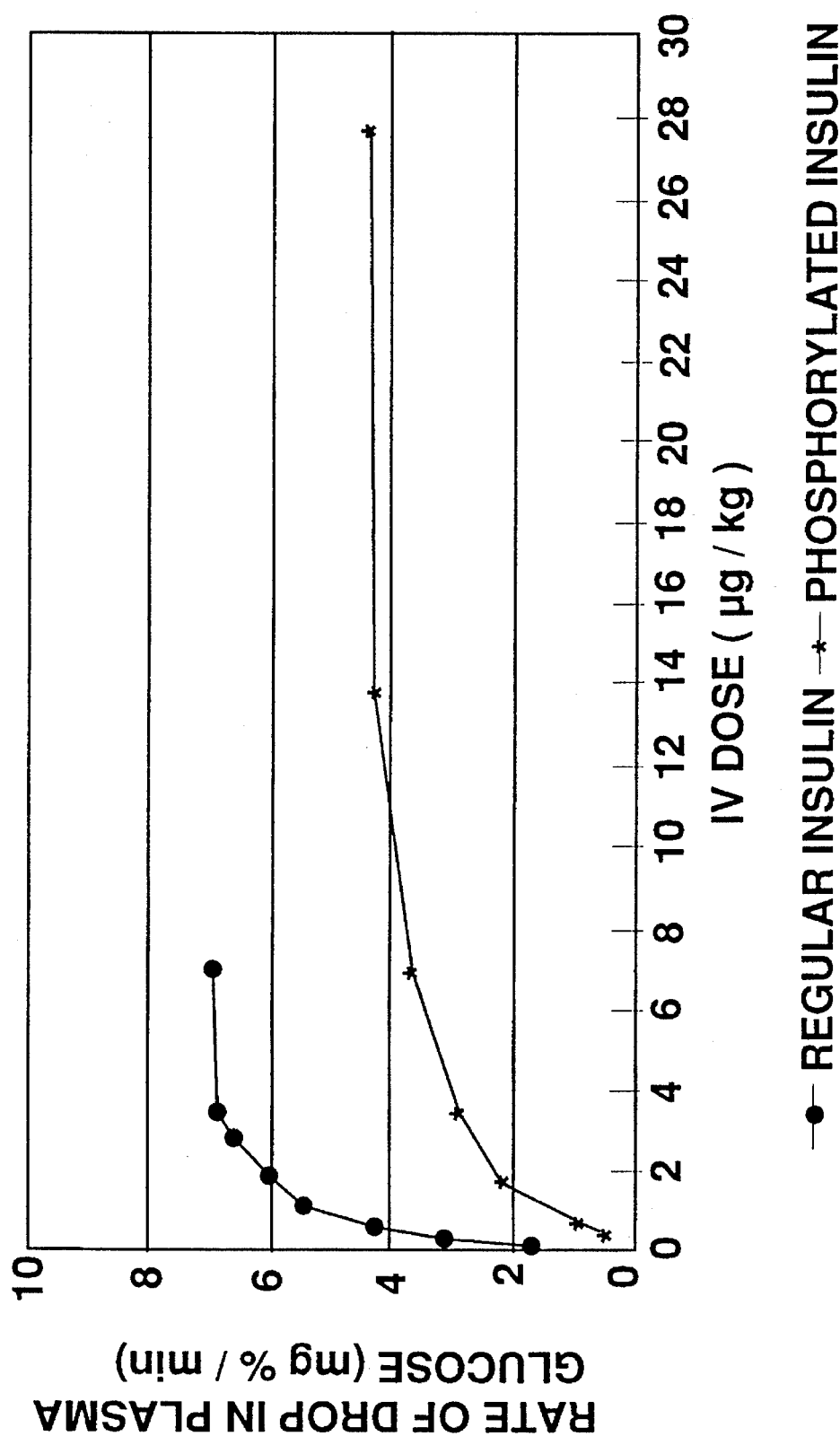
FIG. 8 shows the rate of fall of blood glucose in the first 15 minutes after an intravenous injection of varying doses of either regular or phosphorylated insulin into normal dogs.

Phosphorylated insulin produced by the process described in Example 2 and regular insulin (Iletin II pure Pork) were injected as an intravenous bolus into 4 normal, fasted, beagle dogs. Each insulin was injected at a wide range of dosage with not more than one experiment on each dog on any given day. The plasma glucose of each dog was measured (YSI) at 2 minute intervals for 15 minutes following the injection and the rate of decline of glucose from normal was determined in this period for each individual insulin dose. The results are shown in FIG. 8. When the data from FIG. 8 are analysed, it can be shown that the % change in insulin dose required to produce a given increase in glucose drop (glucose disposal) is greater for phosphorylated than for regular (unmodified) insulin. Thus, for example, in Table 4, a 28% increase in dose of regular insulin from that which produced a glucose drop of 3.5 mg %/min., caused the "rate of drop of glucose" to increase from 3.5 to 4.0 mg %/min. A 66% increase in dose of phosphorylated insulin was required to produce the same effect. This indicates that: 1) variations in the dose of regular insulin produce significantly larger changes in the net rate of net glucose disposal than does phosphorylated insulin (for example, when given at an equally potent dose), 2) this holds true over the entire dose range that was studied, as shown in Table 4.

TABLE 4

| Change In Rate of Drop of Glucose (mg %/min) From To | Required % Increase In Regular Insulin Dose | Required % Increase In Phosphorylated Insulin Dose |
| --- | --- | --- |
| 1.0–1.5 | 49 | 63 |
| 1.5–2.0 | 33 | 68 |
| 2.0–2.5 | 25 | 64 |
| 2.5–3.0 | 20 | 56 |
| 3.0–3.5 | 39 | 50 |

TABLE 4-continued

| Change In Rate of Drop of Glucose (mg %/min) From To | Required % Increase In Regular Insulin Dose | Required % Increase In Phosphorylated Insulin Dose |
| --- | --- | --- |
| 3.5–4.0 | 28 | 66 |
| 4.0–4.5 | 34 | 165 |

This Table shows the % by which the dose of insulin needed to be increased to provide the change in the rate of drop of glucose indicated in the left hand column of this Table.

EXAMPLE 33

Two diabetic dogs were fed a single daily meal of 1100 kcal at 2:00 p.m. daily and given regular (i.e. fast acting) insulin at meal time.

In addition, dogs were infused continuously, 24 hours per day with either regular or phosphorylated insulin (product prepared as example 6).

During repeated experiments the minimum insulin infusion rate required to produce a mean 8 a.m. fasting plasma glucose of 95 mg % was determined for each insulin.

Once this rate was defined, the insulin infusion rate was incrementally increased on each subsequent day until an 8:00 a.m. fasting plasma glucose of 65–75 mg % was obtained (maximum range of 3 consecutive days).

Figure 12:
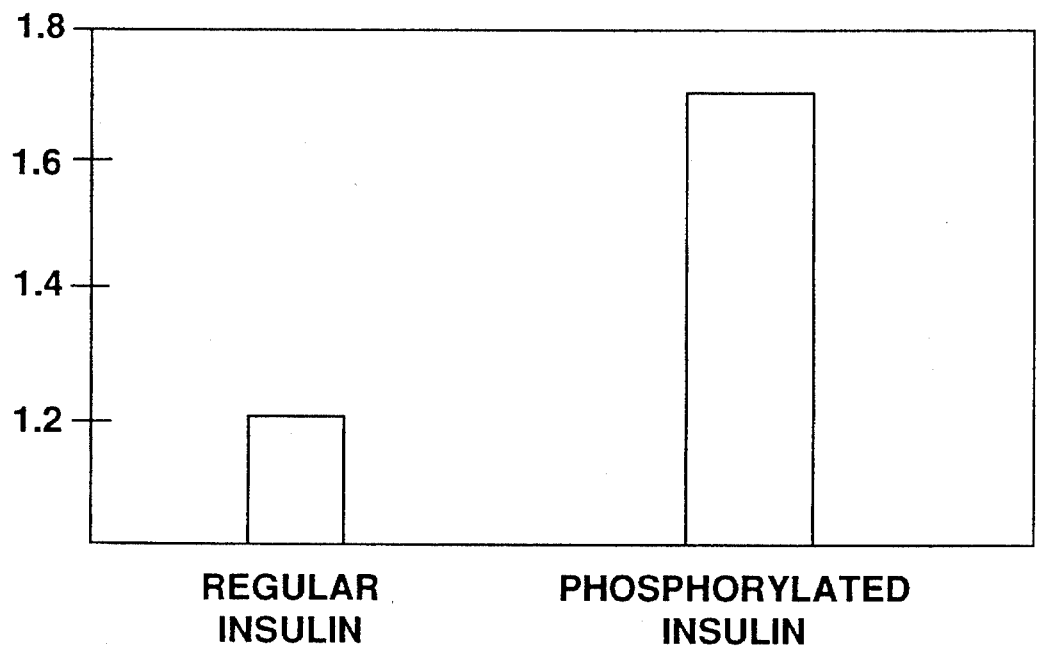

As shown in FIG. 12, the insulin infusion rate for this phosphorylated insulin required a 70% increase in order to drop the fasting glucose from 95 to 70 mg % whereas an increase of only 20% was required with regular insulin. The physiological effect of the flatter dose response described in the last three examples may in whole or in part explain the superior glucose control obtained with the phosphorylated insulins described therein.

I claim:

1. A process for phosphorylating an insulin comprising:
   a) mixing an aqueous solution of said insulin with an amount of phosphorous oxychloride effective to phosphorylate said insulin in the solution under conditions favoring phosphorylation of said insulin,
   b) said conditions including maintaining the aqueous solution at a temperature in the range of 2° to 4° C. and at a pH in the range of 2 to 10 for a time sufficient to produce an insulin essentially free of unmodified insulin.

2. A process as defined in claim 1 wherein the pH is in the range of 6.9 to 9.5.

3. A process as defined in claim 1 wherein the aqueous solution of insulin with the phosphorous oxychloride is maintained for a time in the range of 15 minutes to 4 hours for effecting phosphorylation of the insulin to produce said insulin essentially free of unmodified insulin.

4. A process as defined in claim 3 wherein dialysis or gel filtration of the phosphorylated insulin is effected against water or suitable buffer for removing trace reactants, impurities and salt and to produce a dialysate or filtrate containing the phosphorylated insulin, lyophilizing said dialysate or filtrate to produce a lyophylate, separating and purifying said lyophylate by at least one of high performance liquid chromatography, ion-exchange chromatography and preparative iso-electric focusing, and subjecting the product therefrom to at least one of gel filtration, dialysis and lyophilization.

5. A process as defined in claim 3 wherein dialysis or gel filtration of the phosphorylated insulin is effected against water or a buffer for removing trace reactants, impurities and salt and to produce a dialysate or filtrate containing the phosphorylated insulin, separating and purifying said dialysate or filtrate by at least one of high performance liquid chromatography, ion-exchange chromatography and preparative iso-electric focusing, and subjecting the product therefrom to a purification process selected from the group consisting of gel filtration and lyophilization.

6. A phosphorylated insulin for use in the treatment of diabetes mellitus wherein said phosphorylated insulin is produced according to the process of claim 1 and has an iso-electric point substantially reduced from the iso-electric point of unmodified insulin and has the property of reducing hyperglycemia while reducing the risk of hypoglycemia.

7. A phosphorylated insulin as defined in claim 6 wherein the iso-electric points are less than four.

8. A phosphorylated insulin produced by the process of claim 1.

9. A phosphorylated insulin produced by the process of claim 3.

10. A phosphorylated insulin produced by the process of claim 4.

11. A phosphorylated insulin for use in the treatment of diabetes mellitus wherein said phosphorylated insulin has a phosphate group substituted on tyrosine residues in said insulin and has the property of reducing hyperglycemia while reducing the risk of hypoglycemia.

12. A phosphorylated insulin as defined in claim 11 wherein said insulin is additionally phosphorylated on a free amino group in said insulin, said free amino group being selected from the group of free amino groups consisting of A1 glycine, B1 phenylalanine, B29 lysine, B22 arginine, and A18, A21, and B3 asparagine.

13. A phosphorylated insulin as defined in claim 12 wherein said insulin is additionally phosphorylated on a threonine residue.

14. A phosphorylated insulin as defined in claim 13 wherein said insulin is additionally phosphorylated on a serine residue.

15. A method of treating diabetes mellitus in a human being, said method comprising:

administering to said human being an effective therapeutic amount of a phosphorylated insulin essentially free of unmodified insulin and having an iso-electric point substantially reduced from the iso-electric point of unmodified insulin whereby hyperglycemia is reduced while reducing the risk of inducing hypoglycemia.

16. A method of treating diabetes mellitus in a human being, said method comprising:

administering to said human being an effective therapeutic amount of a phosphorylated insulin produced according to the process of claim 1.

17. A method of treating diabetes mellitus in a human being, said method comprising:

administering to said human being an effective therapeutic amount of a phosphorylated insulin which is essentially free of unmodified insulin and has an iso-electric point substantially reduced from the iso-electric point of unmodified insulin, said administering step is selected from the group consisting of subcutaneous injection, intravenous infusion, and injection, intranasally or rectally.

18. A method as defined in claim 16 wherein the administering step is effected by subcutaneous injection.

19. A phosphorylated insulin for use in the treatment of diabetes mellitus wherein said phosphorylated insulin has a phosphate group substituted on serine residues in said insulin and has the property of reducing hyperglycemia while reducing the risk of hypoglycemia.

20. A phosphorylated insulin for use in the treatment of diabetes mellitus wherein said phosphorylated insulin has a phosphate group substituted on threonine residues in said insulin and has the property of reducing hyperglycemia while reducing the risk of hypoglycemia.

21. A process as defined in claim 1 wherein the pH is in the range of 6.5 to 9.5.

* * * * *